United States Patent [19]
Van Wijck et al.

[11] Patent Number: 5,716,429
[45] Date of Patent: Feb. 10, 1998

[54] METHOD FOR THE SEPARATION OF IMPURITIES FROM A HOT SYNTHESIS GAS MIXTURE IN THE PREPARATION OF MELAMINE

[75] Inventors: Julius G. T. Van Wijck, Maastricht; Cornelis G. M. Van De Moesdijk, Spaubeek, both of Netherlands; Johan J. G. Thoelen, Riemst, Belgium

[73] Assignee: DSM N.V., Heerlen, Netherlands

[21] Appl. No.: 702,871

[22] Filed: Aug. 26, 1996

Related U.S. Application Data

[63] Continuation of PCT/NL95/00086, Mar. 7, 1995.

[30] Foreign Application Priority Data

Mar. 15, 1994 [BE] Belgium ................ 9400281

[51] Int. Cl.[6] ............ C22C 1/04; B01D 46/00
[52] U.S. Cl. ............ 95/273; 55/523; 422/255; 544/203
[58] Field of Search ............ 95/273; 55/523; 210/510.1; 544/201, 203; 422/255, 267, 176, 234

[56] References Cited

U.S. PATENT DOCUMENTS

| | | | |
|---|---|---|---|
| 2,768,144 | 10/1956 | Sundback | 55/523 |
| 3,377,350 | 4/1968 | Watson et al. | 544/201 |
| 4,591,644 | 5/1986 | Leerschool et al. | 544/201 |
| 4,758,272 | 7/1988 | Pierotti et al. | 55/523 |
| 5,497,620 | 3/1996 | Stobbe | 55/523 |
| 5,505,757 | 4/1996 | Ishii | 55/523 |

FOREIGN PATENT DOCUMENTS

| | | | |
|---|---|---|---|
| 331885 | 9/1989 | European Pat. Off. | 55/523 |
| 2-175803 | 7/1990 | Japan | 55/523 |
| 1153107 | 5/1969 | United Kingdom . | |

*Primary Examiner*—Duane S. Smith
*Attorney, Agent, or Firm*—Cushman Darby & Cushman IP Group of Pillsbury Madison & Sutro, LLP

[57] ABSTRACT

Disclosed is an improved method for separating impurities from a hot synthesis gas mixture which is obtained in the preparation of melamine and urea. The improved separation is achieved by use of filters made of sintered, essentially pure chromium, molybdenum, tungsten, or a mixture of any of these elements.

8 Claims, No Drawings

METHOD FOR THE SEPARATION OF IMPURITIES FROM A HOT SYNTHESIS GAS MIXTURE IN THE PREPARATION OF MELAMINE

This is a Continuation of International Appln No. PCT/NL95/00086 filed Mar. 7, 1995 which designated the U.S.

BACKGROUND OF THE INVENTION

1. Field of the Invention

The invention relates to an improved method for the separation by means of filters of impurities from a hot synthesis gas mixture obtained in the preparation of melamine from urea, wherein the improvement is the filters comprising at least one element selected from the group consisting of chromium, molybdenum, and tungsten.

2. Description of the Related Art

Hot synthesis gas mixtures containing nitrogen-based or carbon-based gas, in general, or ammonia or carbon dioxide gas, in particular, or mixtures thereof, are obtained in the preparation of melamine from urea, in which the starting material urea is converted into a hot gas mixture containing melamine, ammonia, and carbon dioxide by the application of heat and, optionally, elevated pressure according to the reaction equation:

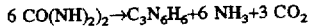

$$6\ CO(NH_2)_2 \rightarrow C_3N_6H_6 + 6\ NH_3 + 3\ CO_2$$

As the above reaction is generally carried out in the presence of a catalyst, the resulting hot synthesis gas mixture will typically contain impurities such as catalyst particles and can also contain other solid byproducts such as melem and/or melam. These impurities are known to have an adverse effect on the quality of the melamine produced.

Known catalysts suitable for use in the above reaction, include among others aluminium oxide, silica-alumina, silicon oxide, titanium oxide, zirconium oxide, boron phosphate, or a mixture of two or more of these catalysts. The term catalyst as it is used herein is defined as any material promoting the conversion of the starting material urea into the final product melamine under the reaction conditions applied.

The hot synthesis gas mixture containing melamine together with ammonia and carbon dioxide gas is formed from the starting material urea at a temperature generally higher than about 325° C. and, in general, not exceeding about 500° C. In particular, temperatures between about 370° and about 450° C. are preferred. The pressure applied during the synthesis of the hot gas mixture in the presence of a catalyst is between about 1 and about 30 bar, preferably between about 1 and about 8 bar.

According to conventional methods of separation, the hot synthesis gas mixture containing melamine, ammonia, and carbon dioxide gas is cooled, and a sublimate of the final product melamine is formed, so that it can be separated from the other gases as a solid. A drawback of this method of separation is that solid catalyst particles and other solid impurities, such as melam and melem, are also separated from the remaining gases along with the melamine sublimate, contaminating the purity of the final product melamine. The solid impurities mentioned above that are separated from the cooled synthesis gas mixture must then be filtered from the desired final product melamine. One known method of separation requires dissolving the formed melamine sublimate in water at a temperature between about 80° C. and about 100° C. The solid impurities which do not dissolve in the water at that temperature are then removed by filtration and an essentially pure final product melamine is obtained by evaporation of the water solvent. A drawback of this method of separation, however, is the number of additional process steps (i.e., cooling the hot synthesis gas mixture, forming the sublimate, separation of the solids from the gases, dissolving the sublimate in solvent, filtering the dissolved sublimate from the undissolved solid impurities, and evaporation of the solvent) that are needed to obtain the essentially pure final product melamine. A second and preferred method of separation therefore, is direct filtration of the hot synthesis gas mixture as the mixture exits reactor. Hot filtration of the synthesis gas mixture saves the time and expense of performing the additional process steps outlined above, which are necessary to obtain an essentially pure melamine final product from a synthesis gas mixture that is allowed to cool before filtration.

One such method of separation of the synthesis gas mixture, by hot filtration through ceramic filters at the reactor outlet, is disclosed on page 11 of NL-A-6412578. Each ceramic filter generally comprises a group of ceramic tubes, which are commonly known as filter candles. Two important aspects of such filter candles for use as filters in the separation methods disclosed above are the individual strength and porosity of the filter candle. The porosity of the filter candle should be between about 20% and about 70%. However, a drawback of utilizing ceramic filter candles is that when these ceramic filter candles come into contact with hot synthesis gas mixtures, the filter-candle strength decreases rapidly and the filter-candles are increasingly susceptible to breakage, for example, due to the temperature surges that occur with the periodical changes in the operation of a synthesis reactor. As a consequence, ceramic filter candles are used only to a very limited extent for separation methods utilizing hot filtration, because the ceramic filter candles have to be replaced after only a few days of use.

Sintered materials, such as for example AISI 304L, AISI 316L, Hastelloy X and Inconel 600, are also materials known for their use as filters in separation methods for synthesis gas mixtures. However, a filter made of a sintered material as described above, when brought into contact with ammonia and carbon dioxide gases, such as those produced in the preparation of melamine from urea, also decreases in strength over a short time owing to the formation of nitrides and/or carbonitrides. As a result of which, these sintered materials are used only to a very limited extent as filters in separation methods for synthesis gas mixtures containing ammonia and/or carbon dioxide gases, becasuse these filters have to be replaced frequently.

SUMMARY OF THE INVENTION

It is an object of the present invention to provide a method for the separation of impurities from hot synthesis gas mixtures, in which filters are used that do not decrease rapidly in strength with temperature surges or due to the formation of nitrides and/or carbonitrides in the presence of ammonia (nitrogen-based) or carbon dioxide (carbon-based) gases.

Although much of the disclosure of the present invention is written in terms of using new filter materials to provide a method for improving the separation of impurities from hot synthesis gas mixtures, for example, improving the known separation by filter of impurities obtained in the preparation of melamine from urea, it is a further object of the present invention to provide a filter device that does not decrease rapidly in strength with temperature surges or due to the formation of nitrides and/or carbonitrides.

These objects are accomplished by the use of filters made of sintered, essentially pure chromium, molybdenum, tungsten, or mixtures of at least two of these elements.

DETAILED DESCRIPTION OF THE INVENTION

In several embodiments of the present invention, mixtures of chromium and molybdenum, chromium and tungsten, molybdenum and tungsten, or a mixture of all three elements can be used, if desired as the filter materials. In a preferred embodiment of the present invention, sintered essentially pure chromium is used. The chromium content of the filter of the present invention, referring to the purity level of the chromium, is in general, at least about 95 wt. %, preferably at least about 99 wt. %, and by special preference at least about 99.8 wt. %. Preferably, use is made of the filters of the present invention in the form of filter candles. These filter candles have, in general, a length of about 0.5 m–2 m and a diameter of about 4 cm–10 cm.

The use of essentially pure chromium in the filters of the present invention is advantageous because the decrease in strength of the filters due to the formation of nitrides and carbonitrides is much slower with chromium than with the many other known filters which utilize metals such as AISI 304L, AISI 316L, Hastelloy X, and Inconel 600. It has been determined that the filters of the present invention can be used for at least a few months, up to a few years, without their strength decreasing to such an extent that the filters break and have to be replaced.

The decreasing strength of filters, which are used in hot filtration methods to separate synthesis gas mixtures containing ammonia and carbon dioxide gas, is primarily a result of the mechanisms of nitriding and/or carbonitriding. Nitriding is caused by, among other things, the presence of ammonia $NH_3$ gas and occurs in particular at temperatures above 250° C. Carbonitriding is caused by, among other things, the presence of carbon dioxide $CO_2$ gas in addition to $NH_3$ gas.

It has been discovered that the filter materials of the present invention, particularly chromium, are remarkably less susceptible to attack by, for example, $NH_3$ and $CO_2$ gas at temperatures above 250° C., than the heretofore known materials utilized in similar filters. As there are other parts of equipment, in general, that can potentially come into contact with $NH_3$ and $CO_2$ gas at temperatures above 250° C., beneficial use can also be made of the material of the present invention, particularly essentially pure chromium, in order to protect these various other equipment parts. Examples, besides reactors for the preparation of melamine, include, without limitation, reactors for the preparation of acrylonitrile, urea, or ammonia. Valves, flanges, reducers, and bends in process lines are some examples, without limitation, of items that are particularly suited for replacement of steel with materials of the present invention, in particular essentially pure chromium.

The improved method of separation according to the present invention is illustrated by the following non-restrictive examples.

EXAMPLE I

A side-stream from a melamine reactor was directed to a pilot reactor where filters containing filter candles, corresponding to Table 1, with a length of 1 m and a diameter of 6 cm, were tested at a temperature of 390° C. and a pressure of 7 bar. Six tests were conducted with each filter containing six filter candles.

The composition of the melamine gas mixture was as follows: 86 vol. % $NH_3$, 8 vol. % $CO_2$, 3 vol. % $N_2$, 3 vol. % melamine and low concentrations of isocyanic acid and cyanide. The pressure drop across the filter housing was used to determine when one or more filter candles had broken. After a pressure drop across the filter housing was observed, the filter housing was immediately opened and the filter was checked to determine how many filter candles had broken. The results of these tests are presented in Table 1.

TABLE 1

| Test No. | Candle type (SiC = silicium carbide) | Number of broken candles | Days of operation before the filter was opened |
|---|---|---|---|
| 1 | SiC candle | 2 | 2 |
| 2 | SiC candle | 6 | 8 |
| 3 | SiC candle | 1 | 4 |
| 4 | SiC candle | 3 | 6 |
| 5 | Chromium candle | 0 | 14 |
| 6 | Chromium candle | 0 | 14 |

EXAMPLE II

Test specimens with the following dimensions were cut from filter candles of various types corresponding to the materials listed in Table 2: length: 50 mm; width: 10 mm, and thickness: 6 mm. The weight of each of the specimens was about 10 grams. The specimens were suspended in an aggressive atmosphere in an exposure furnace at a temperature of 390° C. and 450° C. and kept there for more than a week. The composition of the agressive gas atmosphere was as follows: 86 vol. % $NH_3$, 8 vol. % $CO_2$, 3 vol. % melamine, 3 vol. % $N_2$ and trace amounts of isocyanic acid and cyanamide. Nitriding of the specimens resulted in a mass increase of the specimens, and was measured as the weight increase of the test specimens in micrograms per square centimeter per hour. The test specimens were cut from filter candles made of sintered chromium, solid chromium and stainless steel (AISI 304L). The results are presented in Table 2.

TABLE 2

Results of the exposure experiments

| Material | Exposure temperature, in °C. | Weight increase, in $\mu g/cm^2/hour$ |
|---|---|---|
| Sintered chromium | 450 | 4.2 |
| Sintered chromium | 390 | 0.25 |
| Sintered chromium | 390 | 0.43 |
| Sintered chromium | 390 | 0.12 |
| Solid chromium | 450 | 0.046 |
| Solid chromium | 450 | 0.097 |
| Stainless steel | 390 | 3.0 |
| Stainless steel | 450 | 15 |

What is claimed is:

1. A method for separating impurities from a hot synthesis gas mixture which comprises filtering a hot synthesis gas mixture which is obtained in the preparation of melamine from urea wherein said filtering a sintered filter is used, said sintered filter consisting essentially of at least one member selected from the group consisting of sintered, essentially pure chromium, molybdenum, and tungsten.

2. The method according to claim 1, wherein said filter consists of sintered, essentially pure chromium.

3. The method according to claim 2, wherein said filter has a chromium content of at least about 99 wt %.

4. The method according to claim 3, wherein said filter has a chromium content of at least about 99.8 wt %.

5. The method according to claim 1, wherein said sintered filters are filter candles.

6. The method according to claim 1, wherein said hot synthesis gas mixture contains melamine, ammonia and carbon dioxide.

7. The method according to claim 1, wherein said filter is sintered, essentially pure, molybdenum.

8. The method according to claim 1, wherein said filter is sintered, essentially pure, tungsten.

* * * * *